United States Patent [19]

Dannan

[11] Patent Number: 5,716,326
[45] Date of Patent: Feb. 10, 1998

[54] METHOD FOR LIFTING TISSUE AND APPARATUS FOR PERFORMING SAME

[76] Inventor: Patrick A. Dannan, 13924 Reflection Cove, Unit 213, Ballwin, Mo. 63021

[21] Appl. No.: 514,784

[22] Filed: Aug. 14, 1995

[51] Int. Cl.$^6$ .................................................. A61B 17/02
[52] U.S. Cl. .................... 600/204; 600/214; 600/215; 606/198
[58] Field of Search .................... 606/1, 190, 191, 606/198, 200; 600/204, 208, 210, 213, 214, 215, 216

[56] References Cited

U.S. PATENT DOCUMENTS

| | | | |
|---|---|---|---|
| 5,152,279 | 10/1992 | Wilk | 600/214 |
| 5,195,505 | 3/1993 | Josefsen | 606/198 |
| 5,199,419 | 4/1993 | Remiszewski et al. | 606/198 |
| 5,289,817 | 3/1994 | Williams et al. | 600/204 |
| 5,339,801 | 8/1994 | Poloyko et al. | 600/214 |
| 5,372,147 | 12/1994 | Lathrop, Jr. et al. | |
| 5,505,689 | 4/1996 | Kramer et al. | 600/215 |
| 5,514,075 | 5/1996 | Moll et al. | 600/204 |
| 5,613,939 | 3/1997 | Failla | 600/204 |

Primary Examiner—Max Hindenburg
Assistant Examiner—Benjamin K. Koo
Attorney, Agent, or Firm—Armstrong, Teasdale, Schlafly & Davis

[57] ABSTRACT

A surgical lifter adapted to engage and lift the skin from the underlying tissue to create a work space in which a surgeon can operate, includes an expandable lifter head comprising at least two blades pivotally connected for relative pivotal movement between a deployed position in which the blades are fanned out, and a collapsed position in which the blades overlap one another; and a lifter shaft adapted to extend through the skin to engage the lifter head inside the body. A method of engaging and lifting the skin from the underlying tissue to create a work space in which a surgeon can operate, includes the steps of introducing under the skin an expandable lifter head comprising at least two blades pivotally connected for relative pivotal movement between a deployed position in which the blades are fanned out to form a surface area to engage the inside surface of the skin, and a collapsed position in which the blades overlap one another to facilitate their insertion into, and removal from, the body; inserting the distal end of a lifter shaft through a puncture wound through the skin, and attaching the distal end of the shaft to the expandable lifter head; fanning out the blades of the expandable lifter head to their deployed position; and pulling the lifter shaft to pull the lifter head against the inside surface of the skin to lift the skin away from the underlying tissue.

19 Claims, 6 Drawing Sheets

5,716,326

METHOD FOR LIFTING TISSUE AND APPARATUS FOR PERFORMING SAME

FIELD OF THE INVENTION

This invention relates to a surgical lifter for lifting the skin away from the surgical site during surgery.

BACKGROUND AND SUMMARY OF THE INVENTION

In some types of surgeries, for example certain neck and abdominal surgeries, the skin is lifted from the underlying tissue to create a work space in which the surgeon can operate. Commonly known techniques include inflation of the area with carbon dioxide. However, gas inflation methods are limited in their use since gas inflation is unsuitable for areas such as the neck where the thorax can collapse, pressure in the cerebrum can increase, and gas can leak into the surrounding delicate tissue. Accordingly, gasless surgical lifters are often used. Current surgical lifters suffer from a number of disadvantages. For example, these lifters can place excessive stress on the tissue being lifted, damaging the tissue and causing post operative pain. In addition, these lifters often require a large incision to insert and remove the lifter and thus are limited in their application.

The surgical lifter of the present invention is adapted to engage and lift the skin from the underlying tissue to create a work space in which a surgeon can operate. Generally the lifter comprises an expandable lifter head having at least two blades pivotally connected for relative pivotal movement between a deployed position in which the blades are fanned out to form a large surface area to engage the inside surface of the skin, and a collapsed position in which the blades overlap one another to facilitate their insertion into, and removal from the body. The lifter also comprises a lifter shaft adapted to extend through the skin to engage the lifter head inside the body and apply a lifting force to the lifter head to engage and lift the skin.

The method of this invention allows the surgeon to engage and lift the skin from the underlying tissue to create a work space in which the surgeon can operate. Generally, this method comprises introducing under the skin an expandable lifter head comprising at least two blades pivotally connected for relative pivotal movement between a deployed position in which the blades are fanned out to form a surface area to engage the inside surface of the skin, and a collapsed position in which the blades overlap one another to facilitate their insertion into, and removal from, the body. The distal end of a lifter shaft is inserted through a puncture wound through the skin. The distal end of the shaft inside the body is attached to the expandable lifter head, and the blades of the expandable lifter head are fanned out to their deployed position. The lifter shaft is then pulled against the inside surface of the skin to lift the skin away from the underlying tissue.

The lifter of the present invention is extremely compact so that it can easily be placed under the skin through a relatively small incision with a minimum of disruption to the skin. The lifter is of very simple construction so that it can be quickly and easily inserted, used, and removed. The lifter provides a large contact area with the skin to minimize the stress applied to the skin. The method of the present invention provides a fast, simple, and reliable way to mechanically lift the skin from underlying tissue to create a space under the skin in which to work.

These and other features and advantages will be in part apparent, and in part pointed out hereinafter. dr

BRIEF DESCRIPTION OF THE DRAWINGS

Corresponding reference numerals indicate corresponding parts throughout the drawings.

DETAILED DESCRIPTION OF THE PREFERRED EMBODIMENTS

Figure 1:
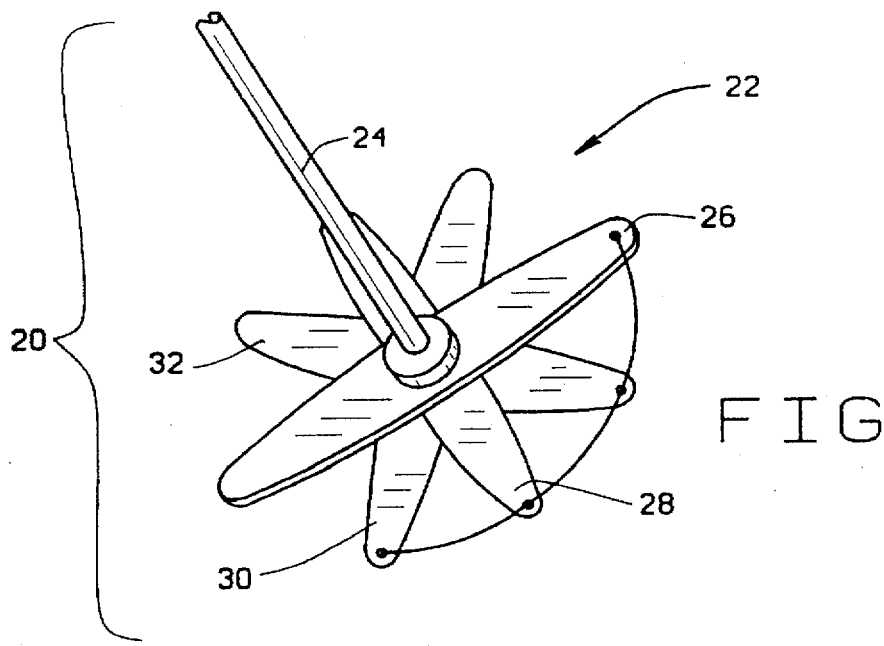
FIG. 1 is a perspective view of a first embodiment of a surgical lifter constructed according to the principles of this invention, shown in its deployed state for lifting the abdominal skin to create a work space in the abdomen.

A first embodiment of the surgical lifter constructed according to the principles of this invention is indicated generally as 20 in FIG. 1. The surgical lifter 20 is adapted to engage and lift the skin from the underlying tissue to create a work space in which a surgeon can operate, as shown in shown in FIGS. 3 and 9. The lifter 20 includes an expandable lifter head 22 and a lifter shaft 24 that engages the lifter head and applies a lifting force to engage and lift the skin.

Figure 2:
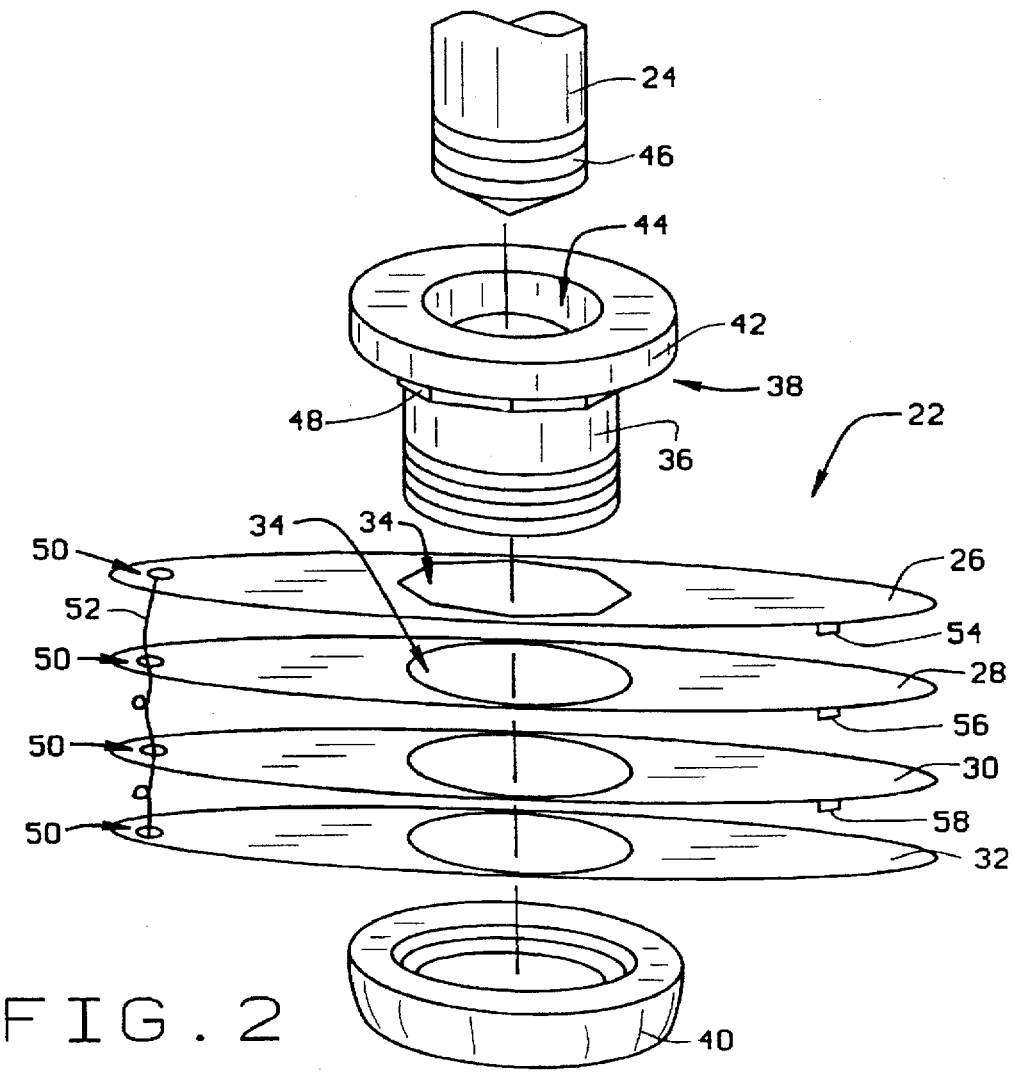
FIG. 2 is an exploded view of the first embodiment, showing its component parts.

The lifter head comprises two or more blades pivotally connected in a stack. In this preferred embodiment there are four blades 26, 28, 30, and 32, pivotally connected together about their mid-points in a stack. As shown in FIGS. 1 and 2, the blades preferably taper from their middles to their ends. The edges of the blades are smooth, and the ends of the blades are rounded to reduce stress concentration to protect the underside of the skin. The blades are preferably all of similar size and shape, except that blade 32 at the bottom of the stack is preferably longer than the other blades to facilitate gripping this blade with forceps, as described below.

Each of the blades has a central opening 34 through which the shaft 36 of a bolt 38 extends. A cap member, such as a nut 40 is secured on the threaded end of the shaft 36 to retain the blades thereon. The blades 26, 28, 30 and 32 can pivot relative to one another for movement between a deployed position, shown in FIG. 1, in which the blades are fanned out to form a large surface area to engage the underside of the skin, and a collapsed position, shown in FIG. 2, in which the blades are generally aligned in a compact stack to facilitate their insertion into, and removal from, the body.

The head 42 of the bolt 38 preferably has a threaded socket 44 therein for receiving the threaded distal end 46 of the lifter shaft 24. In this preferred embodiment one of the blades is keyed to the bolt to turn with the bolt, to facilitate fanning out the blades to their deployed positions. In this first preferred embodiment, blade 26, at the top of the stack is keyed to the bolt 38. As shown in FIG. 2, the opening 34 in the blade 26 has a generally octagonal configuration that engages a generally octagonal collar 48 on the bolt 38 so that the bolt and the blade 26 turn together. Alternatively, the bottom blade 32 could be keyed to the nut and shaft, as described below, in which case the top blade 26 could be made longer to be engaged by forceps.

There is preferably an opening 50 at one end of each of the blades, for tethering adjacent blades with a filament 52. Because the blades are tethered together, anchoring blade 32 at the bottom of the stack, for example with forceps, allows the blades to be fanned out to their deployed position simply by rotating the shaft 24, which rotates blade 26 at the top of the stack. As the shaft 24 rotates, the blade 26 turns, separating the blades 26, 28, and 30 from the anchored blade 32.

The blade 26 at the top of the stack may include a tab 54 for engaging blade 28 adjacent to it in the stack, blade 28 may include a tab 56 for engaging blade 30 adjacent to it in the stack, and blade 32 may include a tab 58 for engaging blade 32 adjacent to it in the stack. The tabs 54, 56, and 58 facilitate collapsing the lifter head 22 from its deployed position. By engaging the blade 32 and rotating the shaft 24 in the opposite direction from the direction used to fan out the blades, the blade 26 pivots over blade 28, and thereafter the tab 54 on blade 26 causes the blades 26 and 28 to pivot together. The blades 26 and 28 pivot over blade 30, and thereafter the tab 56 on blade 28 causes the blade 30 to pivot with blades 26 and 28. The blades 26, 28, and 30, pivot over blade 32, and the tab 58 on blade 30 engages blade 32, which is held securely, preventing further rotation of the blades. Thereafter, further turning of shaft 24 unthreads the distal end of the shaft from the socket 44.

Figure 2A:
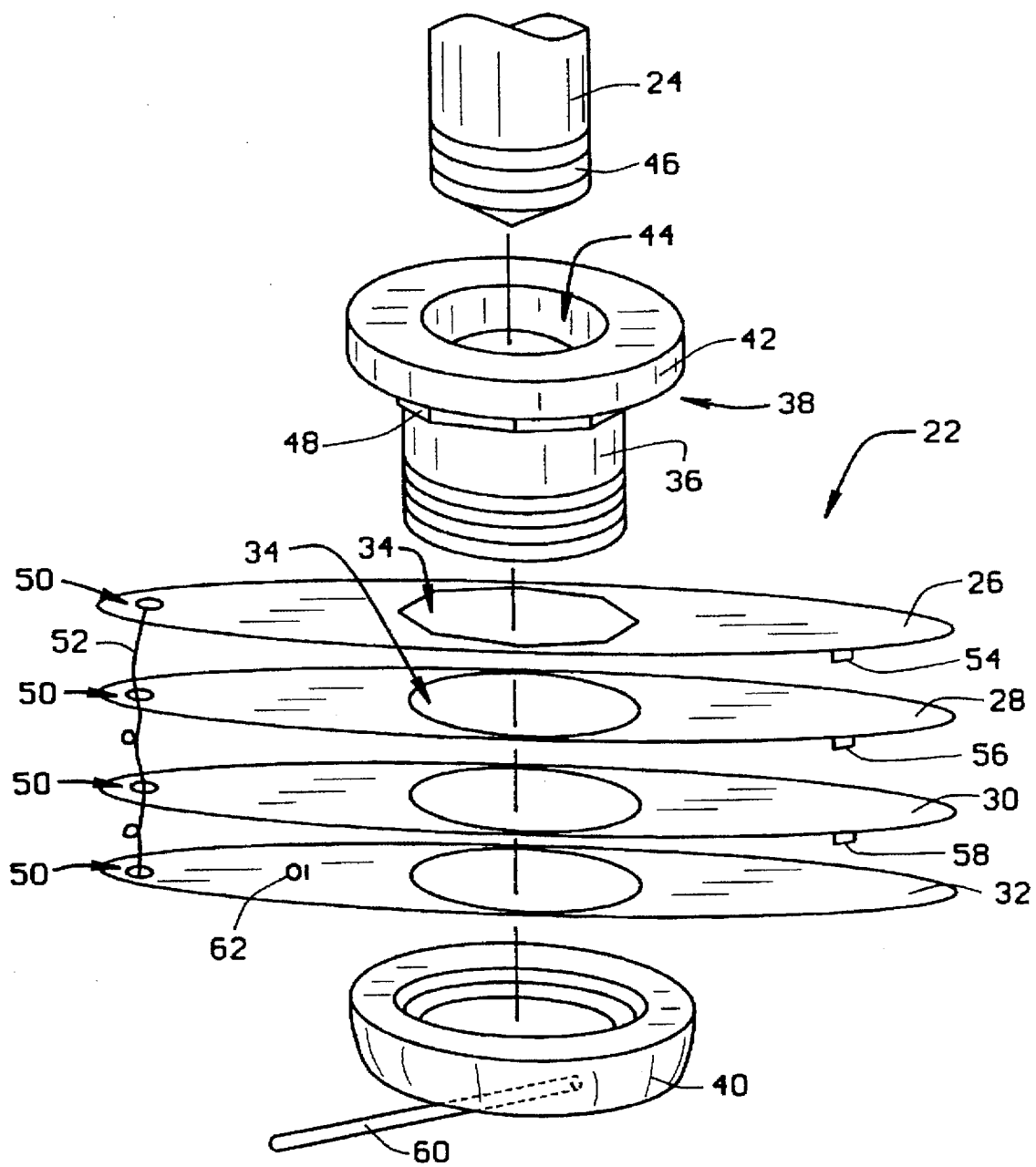
FIG. 2A is an exploded view of an alternative construction of the first embodiment with a spring for resiliently biasing the blades to their deployed position.

As shown in FIG. 2A, the lifter head 22 may optionally include a spring 60 for resiliently biasing the blades to their deployed position. The spring 60 may be mounted on nut 40 and engaged in a catch 62 on blade 32 at the bottom of the stack. The force of the spring 60 biases the blade 32 to rotate relative to the bolt 38 and nut 40. Because the blades are tethered together, the rotation of the blade 32 also rotates blades 30 and 28 relative to blade 26, which is keyed to the bolt 38. Thus the spring 60 resiliently biases the blades to their deployed positions.

Figures 6, 7:
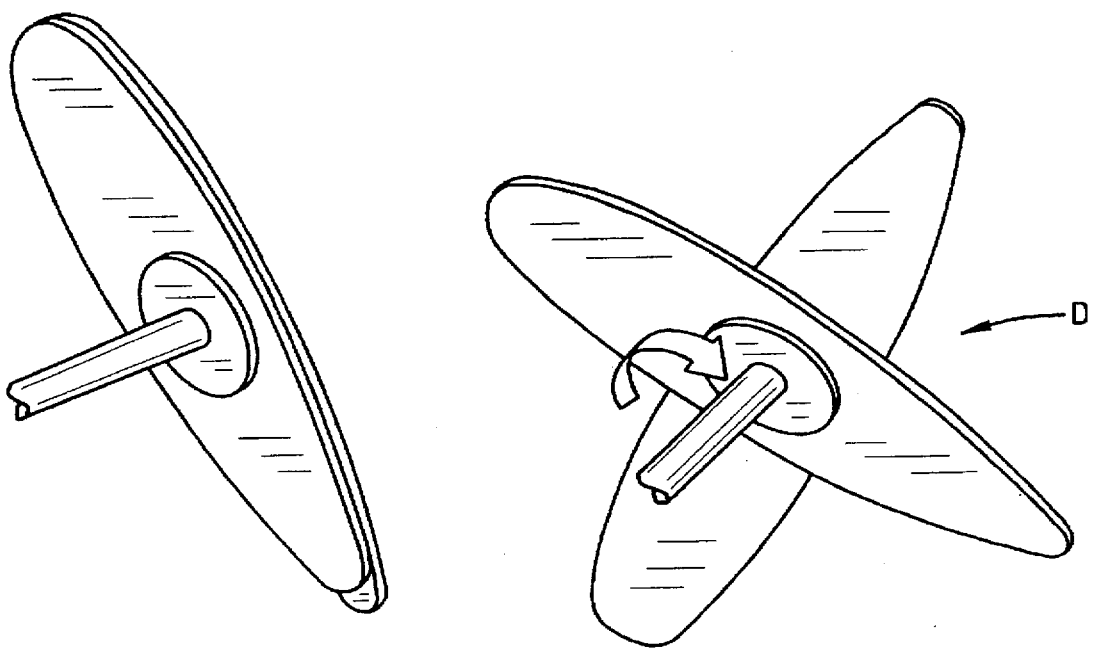
FIG. 6 is a perspective view of a second embodiment of a surgical lifter constructed according to the principles of this invention, shown in its collapsed position.
FIG. 7 is a perspective view of the second embodiment, shown in its deployed position.
Figure 8:
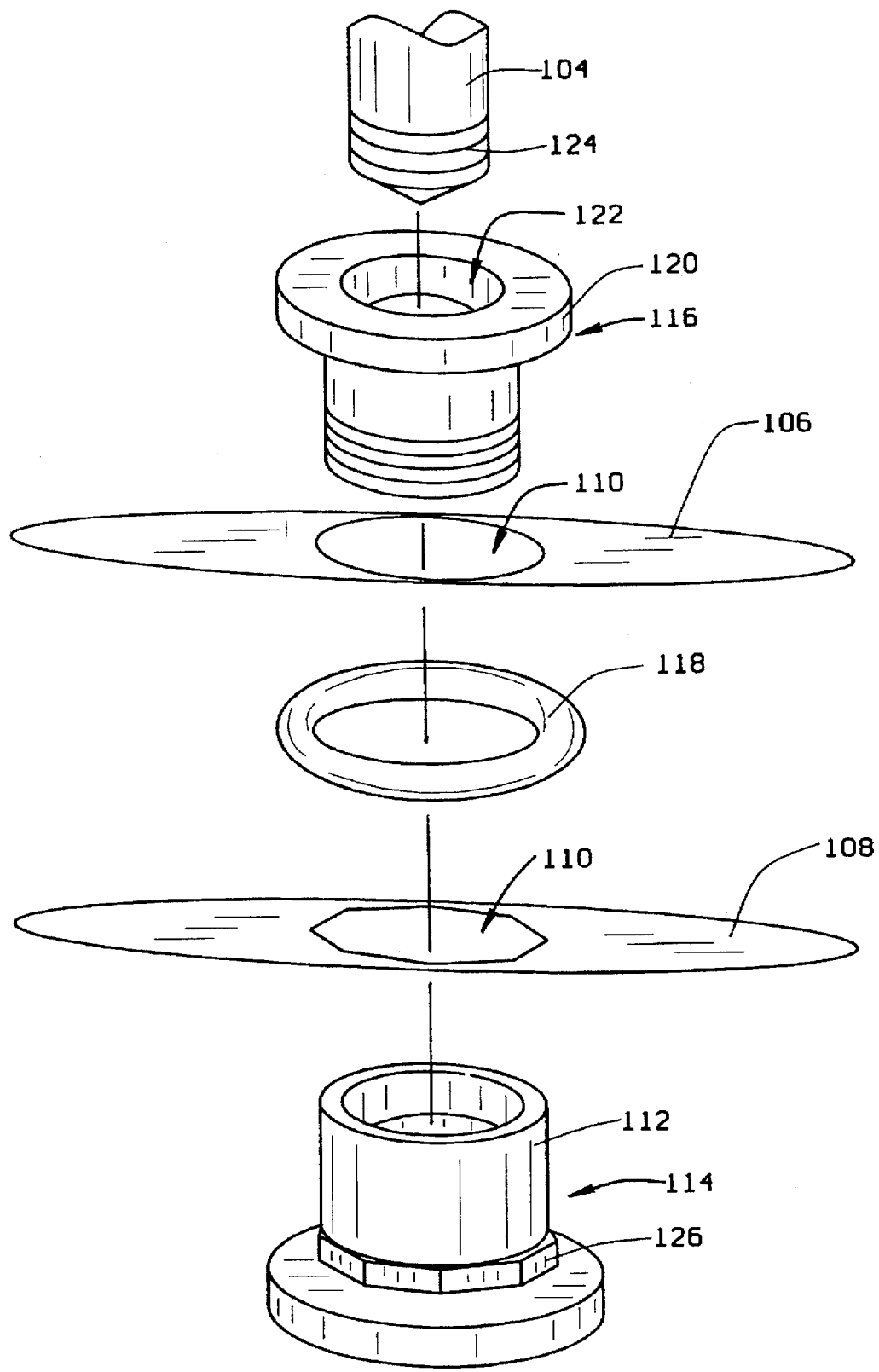
FIG. 8 is an exploded view of the second embodiment, showing its component parts.
Figure 9:
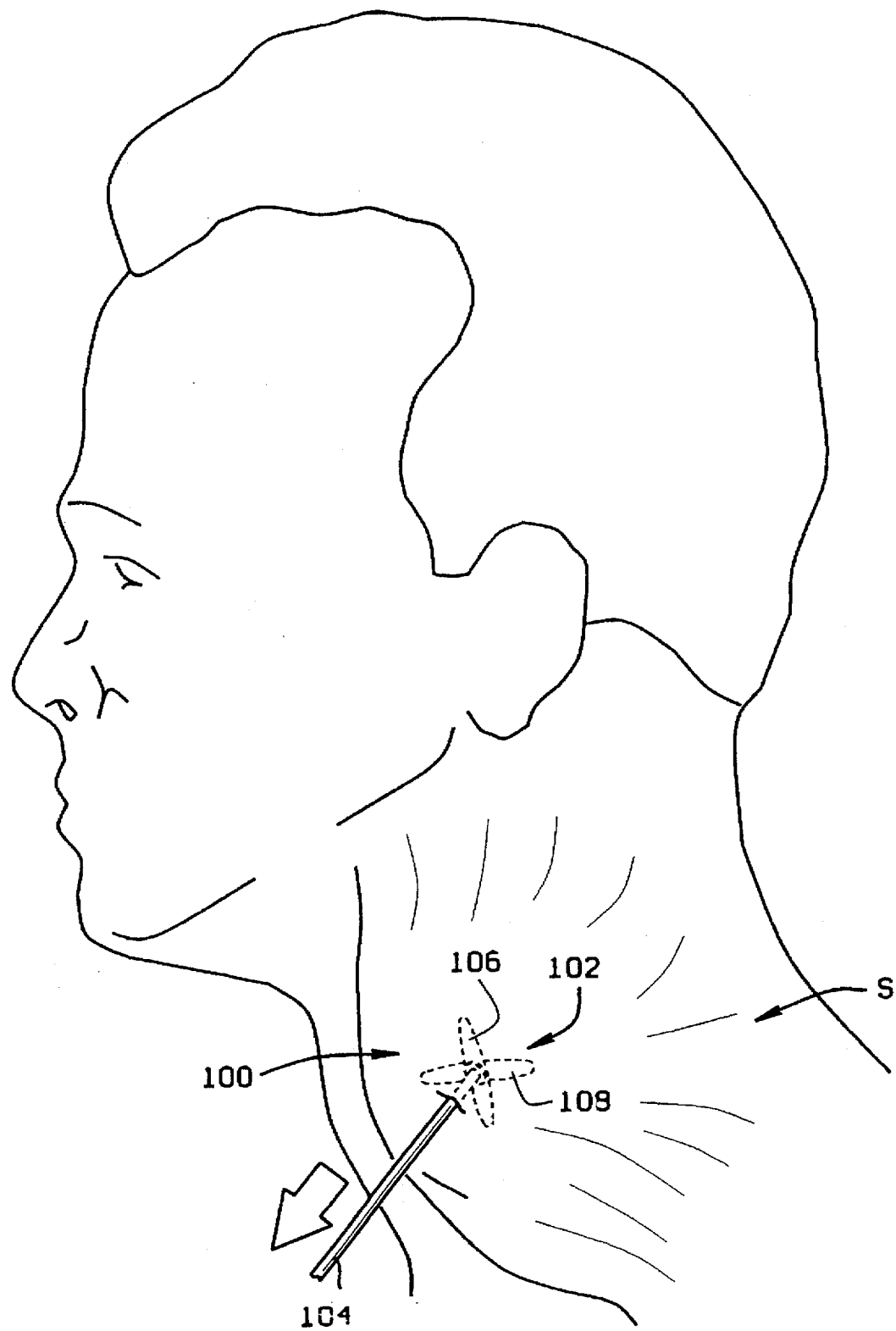
FIG. 9 is a perspective view of a patient's neck, showing how a lifter of the second embodiment would be deployed to lift the skin of the neck to create a work space in the neck.

A second embodiment of the surgical lifter constructed according to the principles of this invention is indicated generally as 100 in FIGS. 6–9. The lifter 100 is particular adapted for use in delicate areas such as the neck where for cosmetic as well as health reasons, the incisions and subsequent scarring should be minimized. Surgical lifter 100 is adapted to engage and lift the skin of the neck from the underlying tissue to create a work space in which a surgeon can operate, as shown in FIG. 9.

The lifter 100 comprises an expandable lifter head 102, and a lifter shaft 104 that engages the lifter head and applies a lifting force to engage and lift the skin. The lifter head 102 comprises two or more blades pivotally connected in a stack. In this preferred embodiment there are two blades 106 and 108, pivotally connected together about their mid-points. As shown in FIGS. 7–9, the blades preferably taper from their middles to their ends. The edges of the blades are smooth, and the ends of the blades are rounded to reduce stress concentration to protect the underside of the skin.

As shown in FIG. 8, each of the blades has a central opening 110 through which the shaft 112 of a cap member such as a T-shaped nut 114 extends. A bolt 116 is threaded into the nut 114 to retain the blades thereon. A spacer 118 is positioned between the blades 106 and 108. The blades 106 and 108 can pivot relative to each other for movement between a deployed position, shown in FIG. 6, in which the blades are fanned out to form a larger surface area to engage the underside of the skin, and a collapsed position, shown in FIG. 7, in which the blades are generally aligned in a compact stack to facilitate their insertion into, and removal from, the body.

The head 120 of the bolt 116 preferably has a threaded socket 122 therein for receiving the threaded distal end 124 of the lifter shaft 104. In this preferred embodiment one of the blades is keyed to the nut 114 to turn with the nut and bolt, to facilitate fanning out the blades to their deployed positions. In this second preferred embodiment, blade 108, at the bottom of the stack is keyed to the nut 114. As shown in FIG. 8, the opening 110 in the blade 108 has a generally octagonal configuration that engages a generally octagonal collar 126 on the nut 114 so that the nut and the blade 108 turn together.

Generally the method of this invention of engaging and lifting the skin from the underlying tissue to create a work space in which a surgeon can operate comprises the steps of introducing an expandable lifter head 22 of the first embodiment, or an expandable lifter head 102 of the second embodiment under the skin with their blades in their respective collapsed position. Then the distal end 46 of the lifter shaft 24, or the distal end 124 of the lifter shaft 104 is introduced through the skin, and secured to its respective expandable lifter head 22 or 102. The blades of the expandable lifter head are then fanned out to their respective deployed position, for example by rotating the shaft 24 or 104. In their deployed positions, the blades are fanned out to form a surface area to engage the inside surface of the skin. A pulling force is then applied to the lifter shaft 24 or 104 to pull the lifter head 22 or 102 against the inside surface of the skin and lift the skin away from the underlying tissue.

After use the lifters 20 and 100 are quickly and easily dissembled by removing the pulling force from the lifter shafts 24 or 104, and rotating the blades to bring the expandable lifter head 22 or 102 to its compact, collapsed position. The distal end of the lifter shaft 24 or 104 can then be detached from the lifter head, and withdrawn from the body. The lifter head can then be removed from under the skin.

OPERATION

Figure 5:
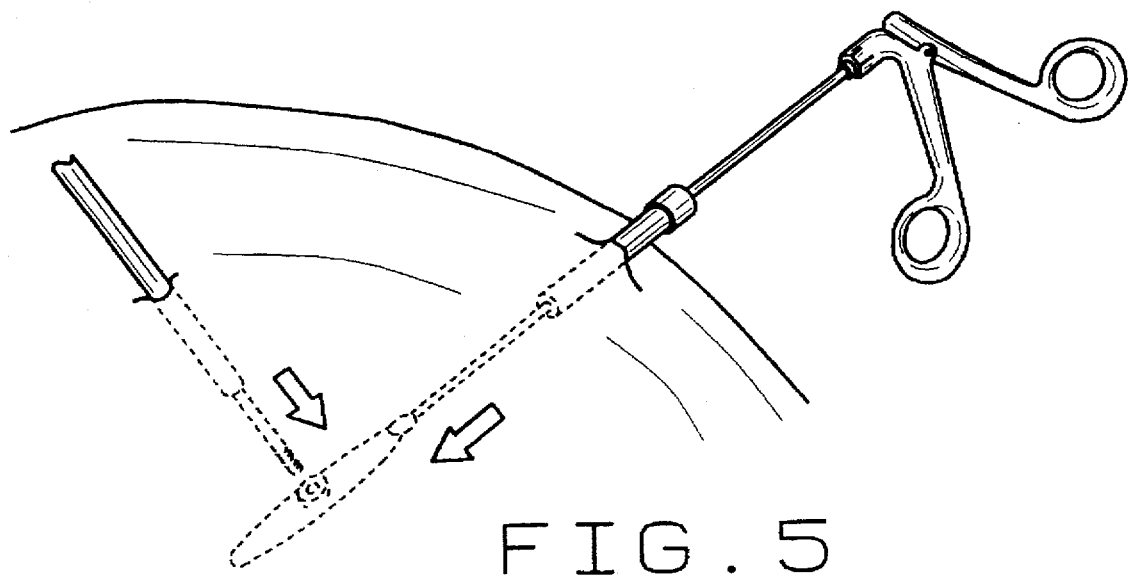
FIG. 5 is a perspective view of a surgical lifter of the first embodiment, showing how the lifter would be assembled and deployed according to the method of this invention.

In operation, the expandable lifter head 22 of the lifter 20 of the first embodiment is introduced into the body, under the skin, through an incision. The expandable lifter head is conveniently introduced into the body with a pair of forceps, as shown in FIG. 5. A puncture wound is then made so that the distal end 46 of the lifter shaft 24 can be inserted though the skin, in the area where the skin is to be lifted. While the lifter head 22 is being held with the forceps, the distal end 46 of the lifter shaft 24 is threaded into the socket 44. Once the end of the lifter shaft is firmly seated in the socket 44, further turning of the shaft causes the blade 26, which is keyed to the bolt 38 to pivot. Because the blades 26, 28, 30, and 32 are all tethered together with filament 52, turning the shaft 24 rotates the blades until the filament is fully extended, and the blades are in their fanned out deployed positions.

Alternatively, with the alternative construction shown in FIG. 2A, the expandable lifter head 22 includes a spring 60 that resiliently biases the blades to their fanned out, deployed positions. In this case the forceps hold the blades together in their generally stacked collapsed position until the lifter shaft 24 is secured to the lifter head 22. Then releasing the forceps allows the spring 60 to fan out the blades to their deployed positions, rotating the blades 32, 30, and 28 relative to blade 26, which is keyed to the bolt 38.

Figure 3:
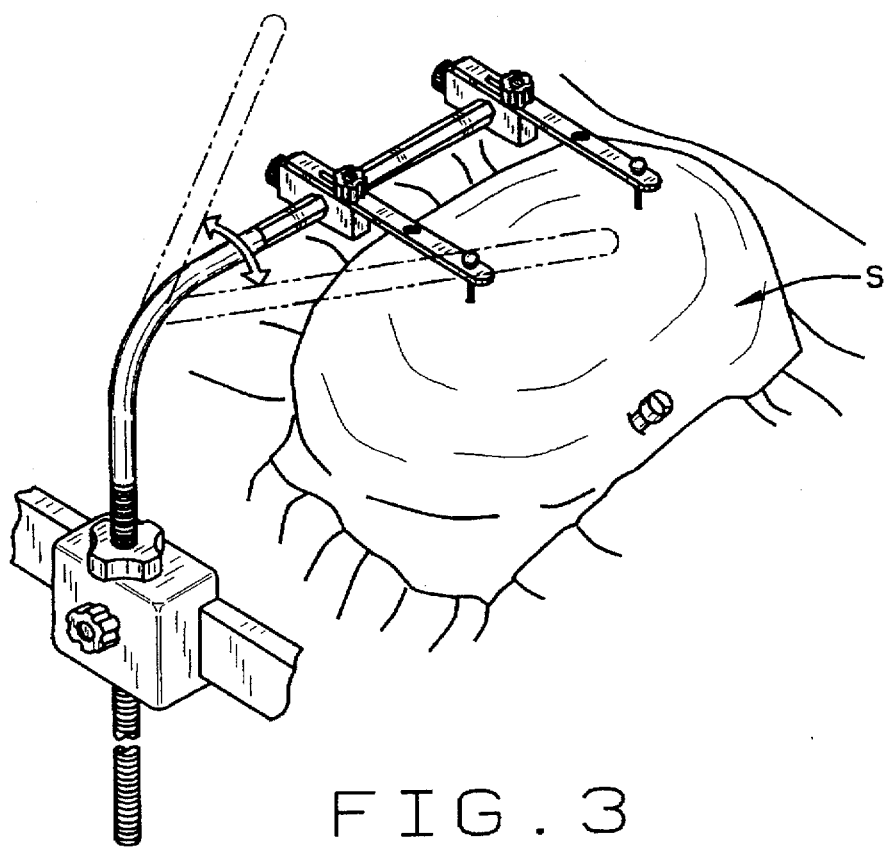
FIG. 3 is a perspective view of a patient's abdomen, showing two lifters of the first embodiment deployed to lift the abdominal skin to create a work space in the abdomen.
Figure 4:
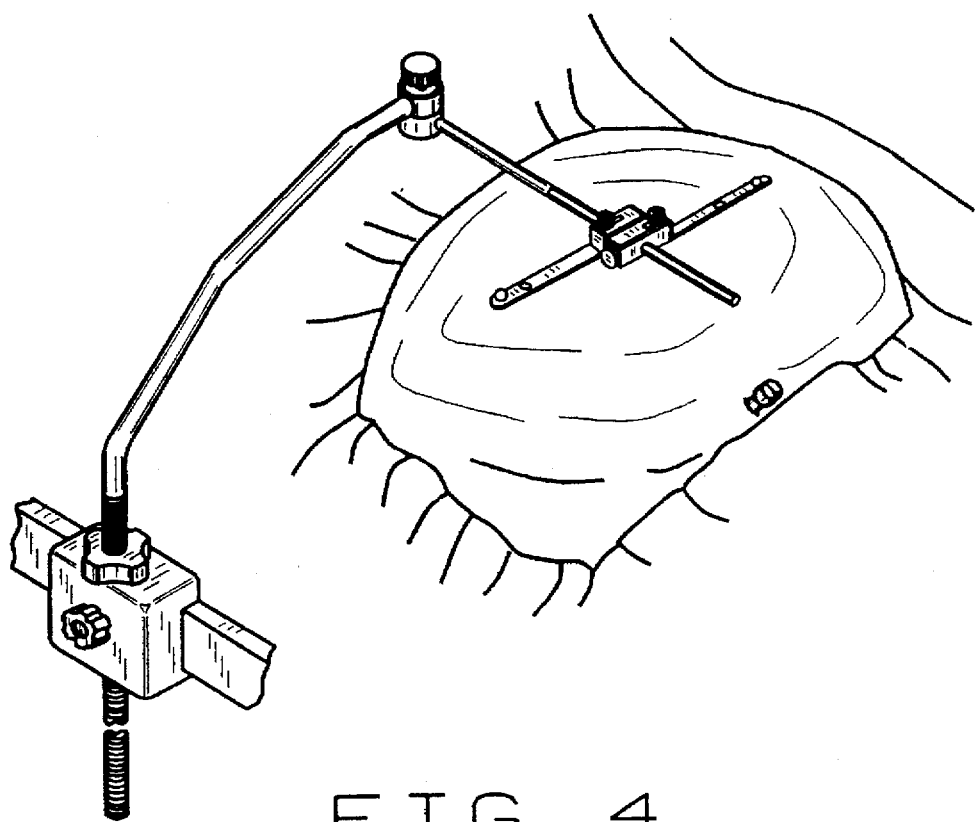
FIG. 4 is a perspective view of a patient's abdomen, showing an alternative way two lifters of the first embodiment could be deployed to lift the abdominal skin to create a work space in the abdomen.

A pulling force is then applied to the lifter shaft 24 to pull the lifter head into contact with the inside surface of the skin, and once the lifter head engages the skin, to lift the skin to create and maintain a work space inside the body in which the surgeon can conduct the surgery. For example the lifter shaft can be secured to a mechanical linkage, as shown in FIGS. 3 and 4, to maintain the pulling force during the surgery.

When the surgery is completed, the pulling force is simply released, and as the skin gradually elastically resumes its pre-surgery configuration, the blade 32 is grasped with the forceps, and the lifter shaft 24 is turned in the opposite direction from which it was turned to fan out the blades. Because the blade 26 is keyed to the bolt 38, as the shaft 24 turns the bolt, the blade 26 rotates over the blade 28 until the tab 54 on the blade 26 engages the blade 28, then the two blades 26 and 28 turn together over the blade 30 until the tab 56 on the blade 28 engages the blade 30, then the three blades 26, 28, and 30 turn together over the blade 32 until the tab 58 on the blade 30 engages the blade 32. Thereafter, further turning of the lifter shaft 24 causes the distal end 46 of the lifter shaft 24 to thread out of the socket 44 in the bolt 38. The distal end of the lifter shaft 24 can then be withdrawn from the body, and the lifter head 22, now in its compact, collapsed position, can be withdrawn from the body through the incision with the forceps.

Similarly, the expandable lifter head 102 of the lifter 100 of the second embodiment is introduced into the body, under the skin, through an incision. The expandable lifter head is conveniently introduced into the body with a pair of forceps, as shown in FIG. 5 with respect to expandable lifter head 22. A puncture wound is then made so that the distal end 124 of the lifter shaft 104 can be inserted though the skin, in the area where the skin is to be lifted. While the lifter head 102 is being held with the forceps, the distal end 124 of the lifter shaft 104 is threaded into the socket 122. Once the end of the lifter shaft is firmly seated in the socket, further turning of the shaft causes the blade 108, which is keyed to the nut 114, to pivot relative to blade 106.

A pulling force is then applied to the lifter shaft to pull the lifter head into contact with the inside surface of the skin, and once the lifter head engages the skin, to lift the skin to create and maintain a work space inside the body in which the surgeon can conduct the surgery. For example the lifter shaft can be secured to a mechanical linkage, as shown with respect to lifter 20 in FIGS. 3 and 4, to maintain the pulling force during the surgery.

When the surgery is completed, the pulling force is simply released, and as the skin gradually elastically resumes its pre-surgery configuration, the blade 106 is grasped with the forceps, and the lifter shaft 104 is turned in the opposite direction from which it was turned to fan out the blades. Because the blade 108 is keyed to the nut 114, as the shaft 104 turns the nut, the blade 108 rotates over the blade 106. As described above with respect to lifter 20, one of the blades 106 or 108 can have a tab or other structure for engaging the other when the blades are aligned in their compact stacked relationship, so that further turning of the shaft 104 causes the distal end 124 of the lifter shaft to thread out of the socket 122 in the bolt 116. Alternatively, the blades can simply be grasped with the forceps to facilitate detaching the distal end 124 of the lifter shaft 104 from the lifter head 102. The distal end of the lifter shaft 104 can then be withdrawn from the body, and the lifter head 102, now in its compact, collapsed position, can be withdrawn from the body through the incision with the forceps.

I claim:

1. A surgical lifter adapted to engage and lift the skin from the underlying tissue to create a work space in which a surgeon can operate, the lifter comprising:

an expandable lifter head comprising at least two blades pivotally connected for relative pivotal movement in a plane between a deployed position in which the blades are fanned out to form a large surface area to engage the inside surface of the skin, and a collapsed position in which the blades overlap one another to facilitate their insertion into, and removal from the body; and a lifter shaft adapted to extend through the skin to engage the lifter head inside the body with the axis of the shaft generally perpendicular to the plane in which the blades pivot and apply a lifting force to the lifter head to engage and lift the skin.

2. The surgical lifter according to claim 1 wherein the blades are pivotally connected generally about their respective mid-points.

3. The surgical lifter according to claim 2 wherein the blades taper toward their ends.

4. The surgical lifter according to claim 3 wherein the ends of the blades are rounded.

5. The surgical lifter according to claim 1 wherein there are four blades.

6. A surgical lifter adapted to engage and lift the skin from the underlying tissue to create a work space in which a surgeon can operate, the lifter comprising:

an expandable lifter head comprising at least two blades pivotally connected for relative pivotal movement between a deployed position in which the blades are fanned out to form a large surface area to engage the inside surface of the skin, and a collapsed position in which the blades overlap one another to facilitate their insertion into, and removal from the body;

a tether extending between adjacent blades to cause the blades to deploy together and collapse together; and a lifter shaft adapted to extend through the skin to engage the lifter head inside the body and apply a lifting force to the lifter head to engage and lift the skin.

7. The surgical lifter according to claim 6 wherein adjacent blades have apertures therein, and wherein the tether comprises a connecting filament threaded through the apertures, the connecting filament for sequentially joining the plurality of lifter blades together.

8. The surgical lifter according to claim 6 further comprising a spring engaging one of the blades for fanning out the blades to their deployed position.

9. The surgical lifter according to claim 8 wherein the spring has a first and second end, wherein the first end of the spring engages to a cap member and the second end of the spring engages to a lifter blade adjacent to the cap member.

10. The surgical lifter according to claim 1 wherein the expandable lifter head is keyed to at least one of the lifter blades to prevent pivoting of the blade relative to the head.

11. The surgical lifter according to claim 1 wherein the lifter shaft threadedly engages the lifter head.

12. The surgical lifter according to claim 1 wherein at least some of the blades have tabs for engaging adjacent blades.

13. A method of engaging and lifting the skin from the underlying tissue to create a work space in which a surgeon can operate, the method comprising:

introducing under the skin an expandable lifter head comprising at least two blades pivotally connected for relative pivotal movement between a deployed position in which the blades are fanned out to form a surface area to engage the inside surface of the skin, and a collapsed position in which the blades overlap one another to facilitate their insertion into, and removal from, the body;

inserting the distal end of a lifter shaft through a puncture wound through the skin, and attaching the distal end of the shaft to the expandable lifter head;

fanning out the blades of the expandable lifter head to their deployed position; and pulling the lifter shaft to pull the lifter head against the inside surface of the skin to lift the skin away from the underlying tissue.

14. The method according to claim 13 wherein the step of fanning out the blades of the expandable lifter head comprises engaging one of the blades and rotating the lifter shaft to rotate the expandable lifter head to fan out the blades.

15. The method according to claim 13 wherein the expandable lifter head includes a spring resiliently biasing the blades to their deployed position; wherein the blades are clamped together while they are introduced under the skin and wherein the step of fanning out the blades of the expandable lifter head comprises releasing the blades to allow them to fan out under the bias of the spring.

16. The method according to claim 13 wherein the blades have tabs for engaging the next adjacent blade, and further comprising the step of collapsing the lifter head to its collapsed position by engaging one of the blades, and rotating the lifter shaft to rotate the expandable lifter head to collapse the blades to overlap the engaged blade.

17. The method according to claim 14 wherein the distal end of the lifter shaft is attached to one of the blades to turn the blade, wherein the blades are tethered adjacent blades, and wherein the step of fanning out the blades of the expandable lifter head to their deployed position comprises engaging one blade and turning the lifter shaft to turn the blade to which it is attached to fan out the blades.

18. A method of engaging and lifting the skin from the underlying tissue to create a work space in which a surgeon can operate, the method comprising:

introducing under the skin an expandable lifter head comprising at least three blades pivotally connected in a stacked relation for pivotal movement between a deployed position in which the blades are fanned out to form a surface area to engage the inside surface of the skin, and a collapsed position in which the blades overlap one another in a stack to facilitate their insertion into and removal from, the body, and tethers connecting the ends of adjacent blades;

inserting the distal end of a lifter shaft through a puncture wound through the skin and attaching the distal end of the shaft to a blade at one end of the shaft;

engaging the blade at the opposite end of the stack from the blade engaged by the lifter shaft, and turning the lifter shaft to fan out the blades.

19. The method according to claim 18 wherein the engaged blade is adjacent to the skin surface.

* * * * *